United States Patent
White et al.

(10) Patent No.: US 9,536,044 B2
(45) Date of Patent: Jan. 3, 2017

(54) METADATA EXTRACTION PIPELINE

(75) Inventors: Steven J. White, Seattle, WA (US);
Sayan D. Pathak, Kirkland, WA (US);
Bryan Dove, Seattle, WA (US);
Duncan P. Robertson, Cambridge
(GB); Khan M. Siddiqui, Highland,
MD (US); Prabhu KrishnaMoorthy,
Redmond, WA (US)

(73) Assignee: Microsoft Technology Licensing, LLC,
Redmond, WA (US)

( * ) Notice: Subject to any disclaimer, the term of this patent is extended or adjusted under 35 U.S.C. 154(b) by 880 days.

(21) Appl. No.: 13/311,570

(22) Filed: Dec. 6, 2011

(65) Prior Publication Data

US 2013/0144907 A1 Jun. 6, 2013

(51) Int. Cl.
*G06F 19/00* (2011.01)
*G06F 17/30* (2006.01)

(52) U.S. Cl.
CPC ....... *G06F 19/321* (2013.01); *G06F 17/30292* (2013.01)

(58) Field of Classification Search
CPC .................................................. G06F 19/321
See application file for complete search history.

(56) References Cited

U.S. PATENT DOCUMENTS

| | | | |
|---|---|---|---|
| 7,587,419 B2 | 9/2009 | Thorpe et al. | |
| 7,826,709 B2 | 11/2010 | Moriya et al. | |
| 7,853,621 B2 | 12/2010 | Guo | |
| 7,889,898 B2 | 2/2011 | Chakraborty et al. | |
| 8,442,321 B1* | 5/2013 | Chang | G06K 9/6202 382/173 |
| 2003/0099385 A1* | 5/2003 | Zeng | G06T 7/0012 382/128 |
| 2006/0069596 A1* | 3/2006 | Hatoun | G06Q 20/108 705/70 |
| 2007/0116337 A1* | 5/2007 | Toth | A61B 6/032 382/128 |
| 2007/0162324 A1* | 7/2007 | Suzuki | G06Q 10/06316 705/7.26 |
| 2008/0080770 A1* | 4/2008 | Mendonca | G06T 7/0087 382/180 |
| 2008/0267471 A1* | 10/2008 | Yu | G06K 9/4604 382/128 |
| 2010/0021027 A1* | 1/2010 | Hartkens et al. | 382/128 |
| 2010/0049740 A1* | 2/2010 | Iwase et al. | 707/104.1 |

(Continued)

OTHER PUBLICATIONS

Lu, et al., "Intelligent Parsing of Scanned Volumes for Web Based Archives", Retrieved at <<http://ieeexplore.ieee.org/stamp/stamp.jsp?tp=&arnumber=4338394>>, International Conference on Semantic Computing (ICSC), Sep. 17-19, 2007, pp. 559-566.

(Continued)

*Primary Examiner* — Jensen Hu
(74) *Attorney, Agent, or Firm* — Jessica Meyers; Tom Wong; Micky Minhas (57) ABSTRACT

An example for processing patient image data workflows can temporarily serially arrange a set of semantic labeling modules in a patient image data workflow pipeline responsive to receiving an event trigger. The example can also remove the set of modules from the patient image data workflow pipeline responsive to receiving an event completion trigger.

18 Claims, 7 Drawing Sheets

(56) References Cited

U.S. PATENT DOCUMENTS

| | | | |
|---|---|---|---|
| 2010/0088644 A1* | 4/2010 | Dowson | G06K 9/3233 715/837 |
| 2010/0114642 A1* | 5/2010 | Dufosse et al. | 705/9 |
| 2010/0223276 A1 | 9/2010 | Al-Shameri et al. | |
| 2010/0268720 A1 | 10/2010 | Spivack et al. | |
| 2011/0010192 A1* | 1/2011 | Backhaus et al. | 705/2 |
| 2011/0022562 A1* | 1/2011 | Gopisetty et al. | 706/48 |
| 2011/0093293 A1* | 4/2011 | G. N. et al. | 705/3 |
| 2011/0110568 A1* | 5/2011 | Vesper et al. | 382/128 |
| 2011/0228995 A1* | 9/2011 | Batman | G06T 19/00 382/128 |
| 2011/0292056 A1* | 12/2011 | Haas | G06F 9/5066 345/505 |
| 2012/0144397 A1* | 6/2012 | Imai et al. | 718/103 |

OTHER PUBLICATIONS

Beno, et al., "AgentMat: Framework for data scraping and semantization", Retrieved at <<http://www.textually.org/textblog/mt_search.php?IncludeBlogs=1&search=germs>>, Third International Conference on Research Challenges in Information Science (RCIS), Apr. 22, 2009, pp. 225-236.

\* cited by examiner

METADATA EXTRACTION PIPELINE

BACKGROUND

Medical imaging technologies, such as x-rays, ultrasound, CT scans, and MRIs, are continually being improved and/or developed. These imaging technologies can produce vast amounts of image data. Sorting through this image data can be overwhelming to clinicians. Automated processing of image data is not readily available since the image data generally is opaque to computers when compared to other forms of patient data. Accordingly, image data remains under-utilized in patient care, among other scenarios.

SUMMARY

The present discussion relates to image data workflows. One example can identify a module configured to generate a metadata output relating to image data. This example can determine other metadata relating to the image data that is used as input by the module. The example can supply the image data to another module that generates the other metadata and direct the other metadata and the image data to the module to generate the output metadata.

Another example can temporarily serially arrange a set of semantic labeling modules in an image data workflow pipeline responsive to receiving an event trigger. The example can also remove the set of modules from the image data workflow pipeline responsive to receiving an event completion trigger.

The above listed examples are intended to provide a quick reference to aid the reader and are not intended to define the scope of the concepts described herein.

BRIEF DESCRIPTION OF THE DRAWINGS

The accompanying drawings illustrate implementations of the concepts conveyed in the present application. Features of the illustrated implementations can be more readily understood by reference to the following description taken in conjunction with the accompanying drawings. Like reference numbers in the various drawings are used wherever feasible to indicate like elements. Further, the left-most numeral of each reference number conveys the Figure and associated discussion where the reference number is first introduced.

DETAILED DESCRIPTION

Overview

This patent relates to a metadata extraction pipeline. The metadata extraction pipeline can provide meaningful input to algorithms operating on image data. Algorithms operating on meaningful input data tend to produce valuable output data. Image data can relate to images of human or animal tissue, hereinafter referred to as "patient image data".

Traditionally, patient image data has been very opaque to automated processing. Stated another way, patient image data has not been interpretable by computers. Accordingly, end users, such as clinicians had to manually sort through and analyze the patient image data. The present concepts can automatically process the patient image data and generate metadata. For instance, the metadata can be in the form of semantic labels or tags of anatomical structures in the patient image data. The semantically labeled patient image data can be further processed to increase the value of the patient image data and/or to produce still further metadata that can be useful for patient treatment, among other uses. Viewed from one perspective, the further processing may be performed on the output of the earlier processing. As such, the patient data can be thought of as passing along a processing pipeline (e.g., the metadata extraction pipeline). Viewed from another perspective, many semantic (and non-semantic) metadata algorithms are made more robust by the presence of other metadata so the metadata extraction pipeline can enable the use of algorithms that depend on other algorithms to function properly.

In some cases, the above concepts can be implemented on a patient image data flow (PIDF) framework that supports executing a set of algorithms in a pre-determined order in the metadata extraction pipeline. The patient image data flow framework can predetermine the order based upon the input requirements and/or the desired output. For instance, assume that a first algorithm utilizes output of a second algorithm as its own input. In such a case, the patient image data flow framework can send the patient image data and patient metadata to the second algorithm and then send the output of the second algorithm and any other input data to the first algorithm. Further, the patient image data flow framework can be agnostic to code (dll's vs. object files). As such, the patient image data flow framework can take any combination of image/non-image data as input and produce any combination of image/non-image data as output.

Use Case Examples

Figure 1:
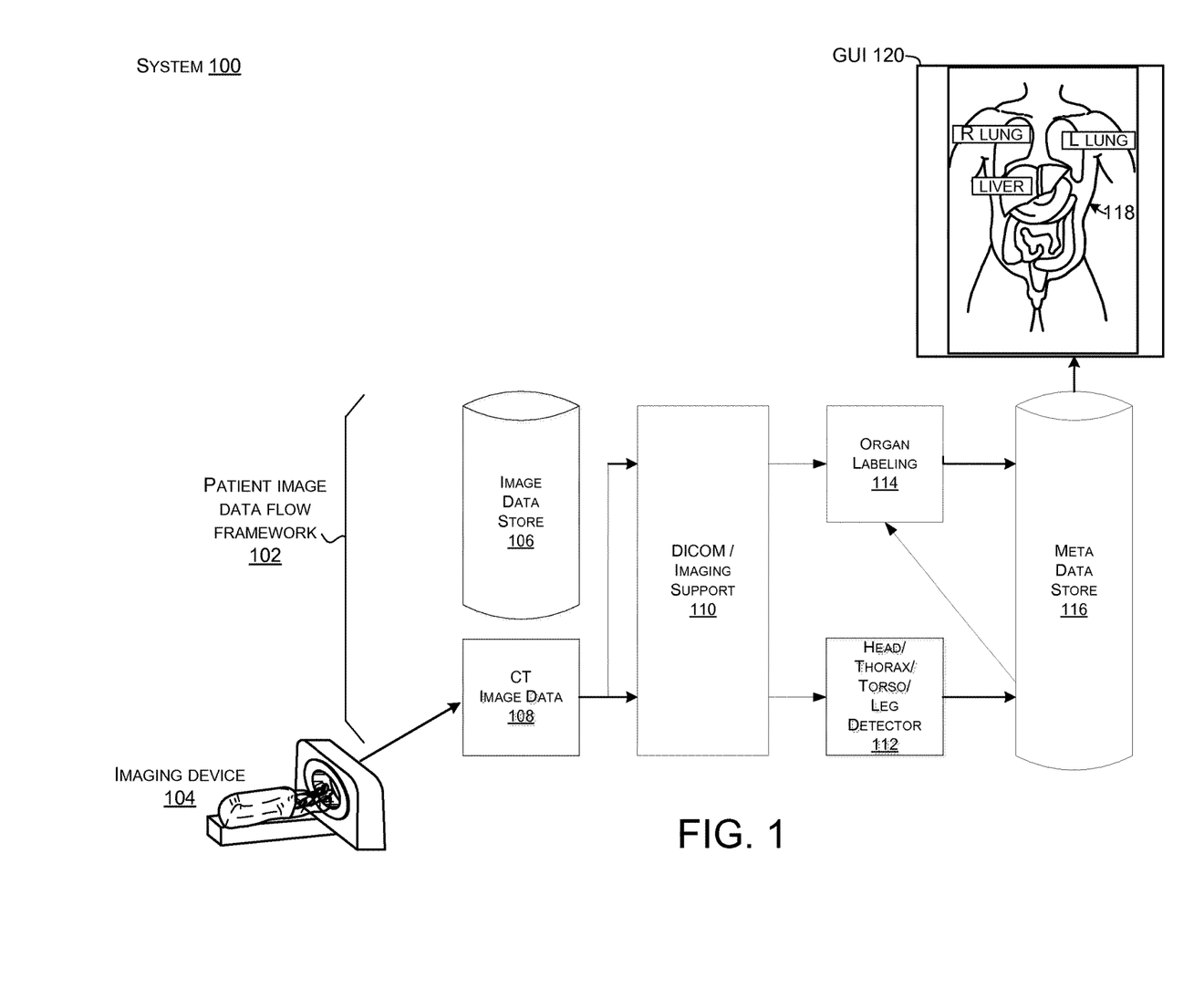
FIG. 1 shows a system upon which patient image data flow framework concepts can be employed in accordance with some implementations.

FIG. 1 shows a system 100 in which a patient image data flow framework 102 can be implemented. In this case, patient image data can be generated by an imaging device 104, such as a CT scanner. In this example, system 100 also includes an image data store 106, full body CT image data 108 received from imaging device 104, a DICOM/imaging support component 110, a head/thorax/torso/leg detector module 112, an organ labeling module 114 and a metadata store 116. Modules are defined in more detail below, but briefly a module can be thought of as an algorithm that can receive patient data and associated metadata and produce a specific output that can include additional metadata.

Assume for purposes of explanation that a clinician, such as a radiologist wants to view a semantically labeled image of the patient's thorax 118 as represented on graphical user interface (GUI) 120. Note that neither head/thorax/torso/leg detector module 112 nor the organ labeling module 114 when operating in isolation can generate the labeled image of the patient's thorax 118 from the full body CT image data 108. The patient image data flow framework 102 can facilitate functioning of the available modules to achieve a desirable result (e.g., in this case the radiologist's request). Toward this end, the patient image data flow framework 102 can first direct the CT image data to the head/thorax/torso/leg detector module 112. The head/thorax/torso/leg detector module 112 can process the full body CT image data 108 to produce an output of semantic tags or labels relating to the patient image data. The output can include metadata in the form of semantic tags that indicate the head, thorax, torso, and leg regions of the patient's full body CT image data 108.

The patient image data flow framework 102 can cause the output (e.g., the semantic metadata) of the head/thorax/torso/leg detector module 112 to be supplied to the metadata store 116 and also to the organ labeling module 114. With this additional input, organ labeling module 114 can accurately semantically tag the organs of the thorax. The organ labeling module 114 can output these semantic tags to the metadata store with the aid of the patient image data flow framework 102. The semantically labeled image of the patient's thorax 118 can be generated from this output. In summary, the patient image data flow framework can provide an imaging service that can facilitate a data workflow pipeline. The data workflow pipeline can be viewed as including serial operation of multiple modules to achieve a cooperative result that could not be obtained from the modules operating on the patient image data alone or in parallel. The modules can be selected and added to the data workflow pipeline in a specific order to achieve a task and removed from the data workflow pipeline when the task is achieved.

Figure 2:
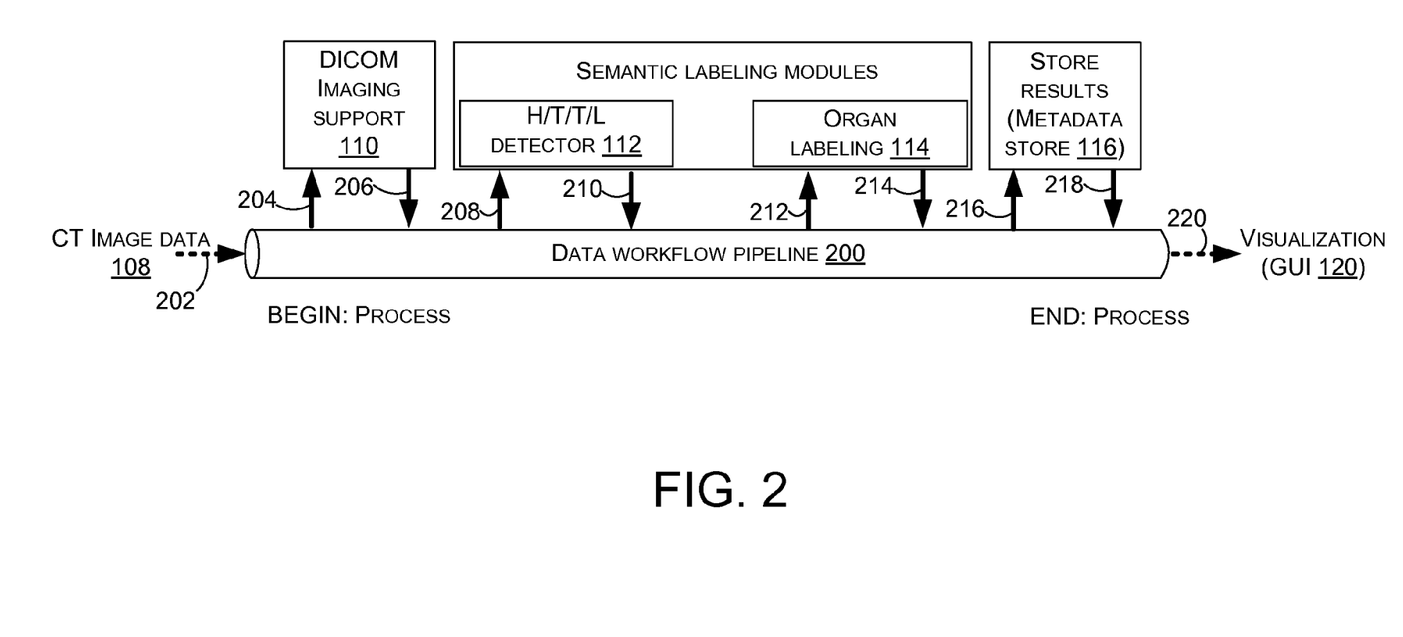
FIG. 2 shows an example of a data workflow pipeline in accordance with some implementations of the present concepts.

FIG. 2 shows a representation of a data workflow pipeline 200 of the processes described above relative to FIG. 1. The data workflow pipeline can be generated or enabled by the patient image data flow framework 102 of FIG. 1, and/or by other components.

The data workflow pipeline 200 can be thought of as a reusable design that can handle scheduling of data processing in a flexible, extensible, and/or modular way. The present example begins by inputting the CT image data 108 into the data workflow pipeline 200 at 202. The data workflow pipeline supplies input CT image data 108 to the DICOM imaging support component 110 as indicated at 204. The DICOM imaging support processing can store the CT image data and any metadata associated with the CT image data. Further, the DICOM imaging support may include other metadata for the patient that can be useful with the CT image data. For example, the CT image data may simply be associated with metadata such as the patient name and the date the image was taken. The DICOM imaging support may include other metadata that may be useful for subsequent stages of the system, such as the patient's age, sex, date that similar CT scans were taken, etc. The DICOM imaging support processing outputs the associated metadata at 206. The DICOM imaging support metadata and the CT image data 108 are supplied to the head/thorax/torso/leg detector module 112 at 208.

The head/thorax/torso/leg detector module 112 can identify the regions (e.g., head, thorax, torso, and leg regions) of the CT image data and semantically tag these regions. These semantic tags can be thought of as metadata which is output by the head/thorax/torso/leg detector module 112 at 210 to the data workflow pipeline 200. This output is obtained by the organ labeling module 114 as indicated at 212. The organ labeling module can use this metadata to focus its search (e.g., the organ labeling module only looks for the liver and lungs in the portion of the CT image data that is labeled as the thorax). The organ labeling module can identify and semantically tag organs within the regions defined by the head/thorax/torso/leg detector and output the semantic tags (and those from the head/thorax/torso/leg detector) as metadata at 214.

The data workflow pipeline can send the metadata from the modules to the metadata store at 216. Metadata can be obtained from the metadata store at 218. This metadata along with the CT image data 108 can be utilized to generate the thorax visualization at 220. In summary, the data workflow pipeline can allow results to be achieved that could not be obtained from any single module. For instance, the efficacy of the organ labeling module operating on the CT image data is relatively poor. However, when the head thorax torso leg detector module and the organ labeling module are serially arranged in the data workflow pipeline, the metadata provided by the head thorax torso leg detector module allows the organ labeling module to focus its analysis of the CT image data to achieve more effective results. Further, the modules can be removed from the pipeline once the results are obtained and the data workflow pipeline 200 can be utilized to achieve another task.

The above discussion provides a detailed example of an on-demand scenario in which the data workflow pipeline 200 can be applied. The data workflow pipeline can give relatively high priority to client requests, such as the visualization request described above. The user wants a timely response so the data workflow pipeline can prioritize previews and organ labels over other tasks so that the user is not left waiting for the visualization.

Examples of other scenarios to which data workflow pipelines can be applied can include study retrieval, proxy creation, ingestion labeling, on demand, cache management policies, such as least recently used (LRU), and semantic registration, among others. Several of these scenarios are discussed in more detail below.

Data workflow pipelines can be utilized in study retrieval scenarios to schedule series requests automatically when another series from a given study is requested. The data workflow pipelines can consider priority in study retrieval scenarios. Often study retrieval is not a top priority where a priority analysis indicates the execution order in a data flow pipeline.

Data workflow pipelines can be utilized in creating compressed versions of the images. In such a case whenever a blob of image data is deleted the data workflow pipeline can schedule creation of a compressed version.

The data workflow pipeline can schedule ingestion labeling of organs to be done whenever a CT scan is received. Ingestion labeling can be given a very low priority (if it doesn't happen by the time a clinician asks for it then the process can be considered an 'on demand' request and given high priority).

In semantic registration scenarios data workflow pipelines can align two different image series (set of images) geometrically using both image content and the semantic information. To execute this process, the data workflow pipeline can define the workflow topology where each of the image series are semantically labeled. Upon completion of the labeling, the data workflow pipeline can take input from the two semantically labeled data sets and align the two images. This can be given a high priority when used in on-demand scenarios and low priority when it happens under ingestion labeling scenarios.

In summary, the data workflow pipeline can provide prioritized execution of multiple tasks executing a process. Further, the data workflow pipeline can handle scenarios where the priority changes while the processes are being executed (e.g., on the fly). Furthermore the data workflow pipeline can allow execution of complex tasks that take many inputs and can produce many outputs that trigger other subsequent tasks as defined in a data workflow topology definition.

The above scenarios include processing, scheduling, prioritization, dependency support (when they should be kicked off) and could benefit from progress reporting and interruptability support—namely dynamic prioritization support. Toward that end, the data workflow pipeline can utilize event triggers that are events external to data workflow logic. Event trigger examples can include data ingestion, user interaction, and/or scheduled events, among others. In the case of date ingestion, the external event could be the arrival of a DICOM image in the patient data flow framework (102, FIG. 1) In the case of user interaction where a user clicks a series of images in a GUI, such as GUI 120, a patient record grid could be used as the triggering external event. A scheduled event can be set up to invoke the data workflow pipeline at a convenient time, such as during the off-peak hours.

The work can be defined for, or by, the data workflow pipeline in various ways. For instance the work can be defined by an imperative definition (e.g., a C# static function). That function could assume that when it is invoked, all dependencies are set (e.g. data table set in database) and could be a single code base that handles all steps for the event. For instance, upon image arrival, the steps could include handling data storage and processing tasks, organ labeling and any study prefetch that may be helpful.

The data workflow pipeline can also offer composability in that data workflow pipeline sub-tasks can be spawned from a single event. The sub-tasks, in turn, could spawn others (e.g., sub-sub-tasks).

Standardized data workflow APIs (or other standardized techniques) can be utilized to invoke the workflow code. For instance, "COM" or "C#" or web services can be utilized, among others. Web services APIs lend themselves to distributed configurations and are easily scalable to a network. In such a case, actions can be invoked across server and process boundaries (e.g., one event won't be isolated to one process).

The image data flow framework can instantiate multiple data workflow pipelines. Individual data workflow pipelines can manage some scarce/limited resource and allocate access/use to that resource based on a stack-ranking of tasks based on task priority. The higher priority tasks can get first access. As these workflows are completed, or interrupted externally, they are de-prioritized. Other events, internal and external, may dynamically change individual priorities. The patient image data flow framework can rapidly and efficiently respond to such status changes and re-order work appropriately.

The data workflow pipeline can employ callbacks or other mechanisms to allow applications to determine the status, and to read or change (e.g. cancel) the priorities of tasks. Further, the data workflow pipeline can allow multiple different algorithms/executables that take specified data, specified parameters, and specified workflow, and allows dynamic execution of different services to generate the desired output.

Figure 3:
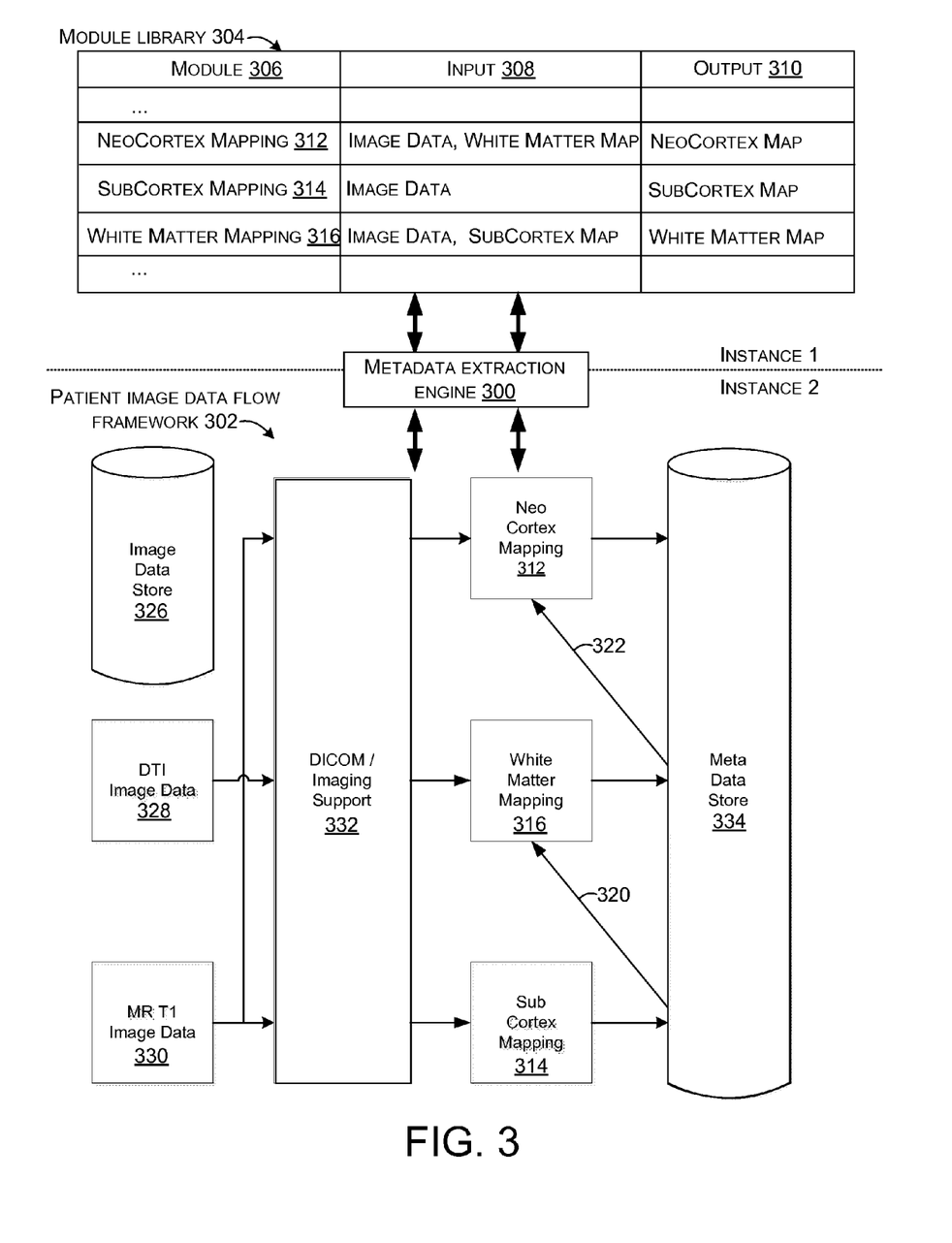
FIG. 3 shows an example of a patient image data flow framework in accordance with some implementations of the present concepts.

FIG. 3 expands on some of the inventive concepts introduced above relative to FIGS. 1-2 by way of another example scenario. In this case, a metadata extraction engine 300 implements a patient image data flow framework 302. For ease of explanation, FIG. 3 is separated into instance 1 and 2.

As illustrated relative to instance 1, the metadata extraction engine 300 can generate or access a module library 304.

The module library contains a listing of modules that can act upon patient image data and/or associated metadata. The metadata extraction engine 300 can select a set of modules from the module library to achieve a task. For sake of brevity only three modules are listed in the module library 304. In this configuration, the module library includes a module column 306 that lists the modules by name, an input column 308, and an output column 310. The input column 308 shows what input is utilized by an individual module. The output column 310 shows what output is produced by the individual module. For instance, a neocortex mapping module 312 is configured to receive as input "image data" and a metadata "white matter map". The neocortex mapping module can process the input data to produce as output a "metadata neocortex map". Similarly, a subcortex mapping module 314 receives "image data" as input and outputs a metadata "subcortex map" and a white matter mapping module 316 can receive "image data" and the metadata "subcortex map" to output a metadata "white matter map".

In various scenarios, the metadata extraction engine 300 may access the module library 304 to facilitate operation of some or all of the modules. For example, a user, such as a clinician may request to view the neocortex map of a patient. In another case, new patient images may be received that cause the metadata extraction engine to begin processing of the image data. In still another example, the metadata extraction engine 300 may run modules when computing resources are available (such as at night when resource usage is lower). In any of these cases, the metadata extraction engine can determine which modules rely on output of other modules and temporarily communicatively couple the modules in a logical order to allow the modules to operate effectively. For instance, continuing with the earlier example, assume that the clinician requests the neocortex map of a patient. The metadata extraction engine can identify in the module library that the neocortex mapping module 312 can generate the neocortex map. The metadata extraction engine can then identify that the neocortex mapping module 312 utilizes a white matter map as input. The metadata extraction engine can then identify that the white matter mapping module 316 can produce the white matter map utilized by the neocortex mapping module 312. Similarly, the white matter mapping module utilizes the subcortex map as input. The subcortex mapping module 314 can produce this subcortex map from image data.

Instance 2 shows how the metadata extraction engine 300 can logically temporarily communicatively couple a set of modules to achieve a specified outcome (in this case a neocortex map). Specifically, in instance 2, the metadata extraction engine 300 communicatively couples the output of the subcortex mapping module 314 to the input of the white matter mapping module 316 as indicated at 320. The metadata extraction engine 300 also communicatively couples the output of the white matter mapping module 316 to the input of the neocortex mapping module 312 as indicated at 322. Stated another way, the modules can be serially arranged so that each module receives appropriate input to achieve its specified output. Viewed from another perspective, the metadata extraction engine 300 can create a direct acyclic dependency graph of module 312, 314, and 316 to process the patient image data. The metadata extraction engine can track what metadata input (e.g., prior) is utilized by each module to process the patient image data and what trigger starts the patient image data workflow processing.

In this example, the metadata extraction engine 300 also communicatively couples the neocortex mapping module 312, the subcortex mapping module 314, and the white matter mapping module 316 to various other components to enable generation of the neocortex map. Specifically, the metadata extraction engine 300 can couple the modules to the image data in image data store 326, DTI image data 328, and MR T1 image data 330. In this case, the image data is channeled through DICOM imaging support component 332 and then to the modules. Output from the modules is also communicated to metadata store 334.

Viewed from another perspective, the metadata extraction engine 300 can be thought of generating a directed graph processor where the modules can be thought of as processing nodes. In this example, the white matter mapping module 316 can be thought of as a child node of the subcortex mapping module 314 and the neocortex mapping module 312 can be thought of as a child node of the white matter mapping module and a grandchild of the subcortex mapping module. In this model the child nodes build on the metadata and image data from their parent node(s).

In summary, patient image data flow framework 302 can be thought of as generic data flow framework that supports executing a set of modules in a pre-determined order in a data workflow pipeline. The patient image data flow framework can be agnostic to code (dll's vs. object files). The patient image data flow framework can take any combination of image/non-image as input. The patient image data flow framework can produce any combination of image/non-image data as output.

Workflow Example

Figure 4:
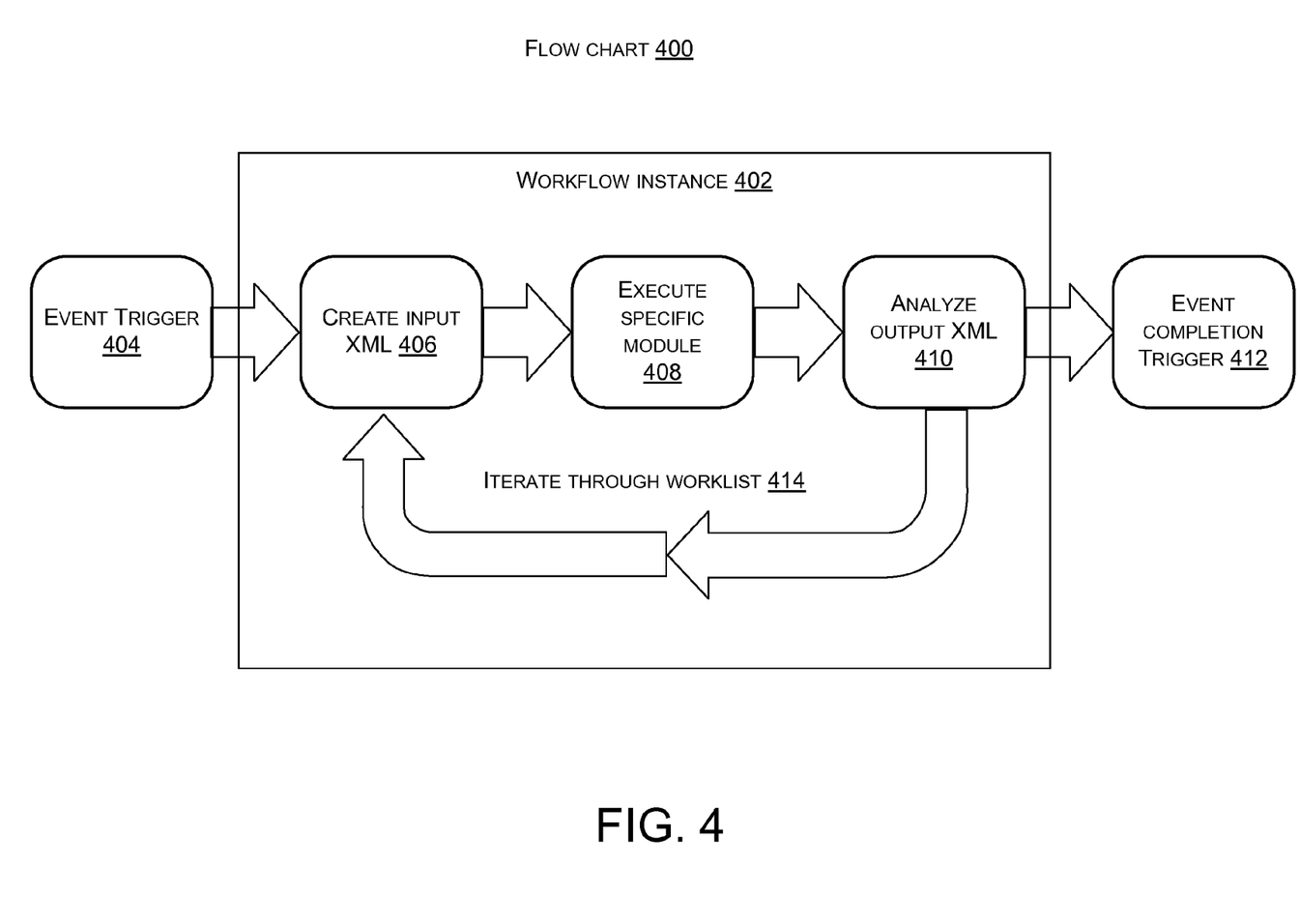
FIGS. 4-6 illustrate examples of flowcharts of data workflow methods in accordance with some implementations of the present concepts.

FIG. 4 shows another characterization of the present concepts as a method flow chart 400. The flow chart relates to a workflow instance 402. Briefly, the flowchart 400 begins when the workflow instance 402 receives an event trigger 404. The workflow instance can create an input XML at 406 based upon the event trigger. The input XML is executed by a specific module at 408 that is configured to utilize the input. The output of the specific module is analyzed at 410. The analysis can lead to an event completion trigger at 412. Alternatively or additionally, the analysis can itself be iteratively used as input through the worklist at 414 to further refine the output.

In some implementations, each workflow can have a specific ID, a priority setting, and a worklist. The worklist can include work items which in turn can point to DLLs, other workflows, and/or SQL scripts. One example is provided below.

```
<Workflow>
    <id>4388</id>
    <name>CT Organ Recognizer</name>
    <priority>High</priority>
    <worklist>
        <workListItem>
            <Name>Read DICOM</Name>
            <Type>DLL</Type>
            <exeURL>(Path to the DLL)</exeURL>
        </workListItem>
        <workListItem>
            <Name>Normalize Data</Name>
            <Type>DLL</Type>
            <exeURL>(Path to the DLL)</exeURL>
        </workListItem>
        <workListItem>
            <Name>Organ Recognizer</Name>
            <Type>Workflow</Type>
            <exeURL>(Path to Workflow XML descriptor)</exeURL>
        </workListItem>
        <workListItem>
```

-continued

```
            <Name>SQL Store</Name>
            <Type>SQLscript</Type>
            <exeURL>(Path to SQL script)</exeURL>
        </workListItem>
    </worklist>
</Workflow>
```

Each work list item can be called a module (introduced above). In some configurations, the module can have three components. First, the module can have an input XML file that specifies all the inputs. Second, the module can have an executable XML that specifies the location of the executable and its type. Third, the module can have an output XML file that specifies all outputs including a path to the log files.

In some configurations, each workflow instance is independently able to create the input files for the specific modules in its work flow list. Further, in the present example, the input and output is via XML but could be inserted via any input/output format.

Various types of event triggers can be employed. For example, triggers can be manual, or can be based upon a condition such as "if % CPU load<x %". The event trigger can also be dependent upon data retrieved from other external systems, such as image storage systems. Recall that some examples were described above relative to FIG. 2.

The triggering mechanism can leverage association of a workflow with the corresponding trigger. The trigger can kick off a workflow by setting an initial input file.

An event completion can trigger an event which synchronously parses the resulting output (in the above example XML) file and takes suitable archival steps. The event completion trigger can asynchronously queue up the output processing requests.

Figure 5:
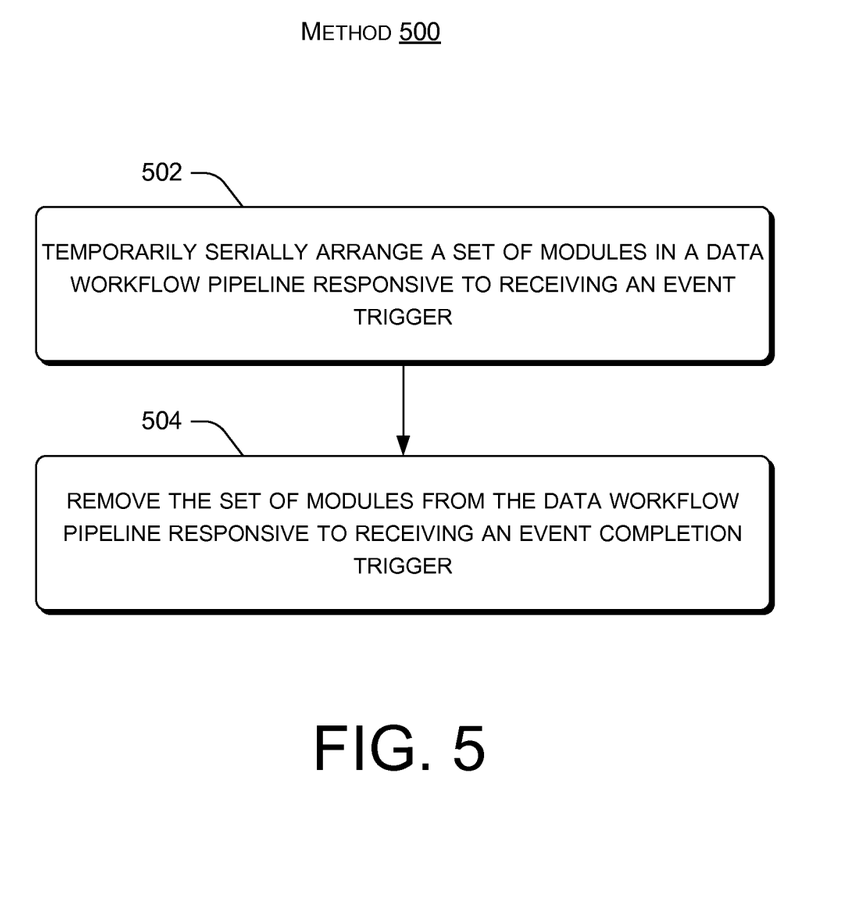

FIG. 5 illustrates a flowchart of another patient image data workflow technique or method 500.

At block 502, the method can temporarily serially arrange a set of modules in a data workflow pipeline in response to receiving an event trigger. The data workflow pipeline can receive patient image data and generate associated metadata, such as by semantically labeling the patient image data. Subsequent portions of the data workflow pipeline can leverage the metadata to create additional metadata.

At block 504, the method can remove the set of modules from the data workflow pipeline in response to receiving an event completion trigger.

In summary, an instance of the data workflow pipeline can be created to collectively accomplish a task with the set of modules. Viewed from one perspective, the data workflow pipeline can take patient image data and metadata ('hints') and produce additional and new metadata (and new image data) with information about the content of the image (e.g. location of organs or pathology) to accomplish the task. For instance, the data workflow pipeline can consume and produce labeled anatomical and pathological region information of the patient image data.

Figure 6:
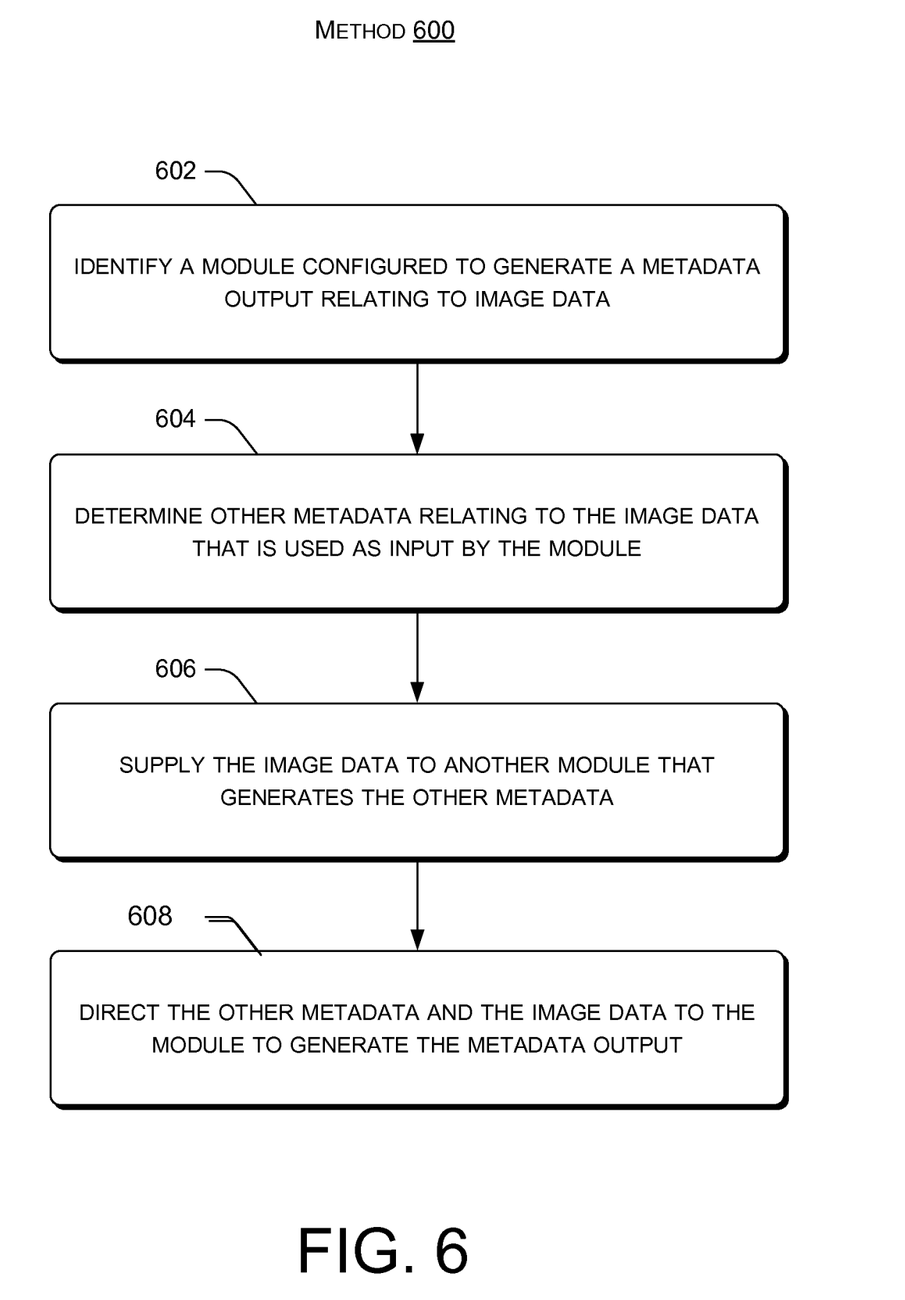

FIG. 6 illustrates a flowchart of another patient image data workflow technique or method 600.

At block 602, the method can identify a module configured to generate a metadata output relating to patient image data.

At block 604, the method can determine other metadata relating to the patient image data that is used as input by the module.

At block 606, the method can supply the patient image data to another module that generates the other metadata.

At block 608, the method can direct the other metadata and the patient image data to the module to generate the output.

To summarize, the method can leverage the fact that many metadata modules are made more robust by the presence of other metadata so the method can enable the use of modules (e.g., in this case "the module") that depend on other modules (e.g., in this case "the another module") to function properly.

The order in which the example methods are described is not intended to be construed as a limitation, and any number of the described blocks or steps can be combined in any order to implement the methods, or alternate methods. Furthermore, the methods can be implemented in any suitable hardware, software, firmware, or combination thereof, such that a computing device can implement the method. In one case, the method is stored on one or more computer-readable storage media as a set of instructions such that execution by a computing device causes the computing device to perform the method.

System Example

Figure 7:
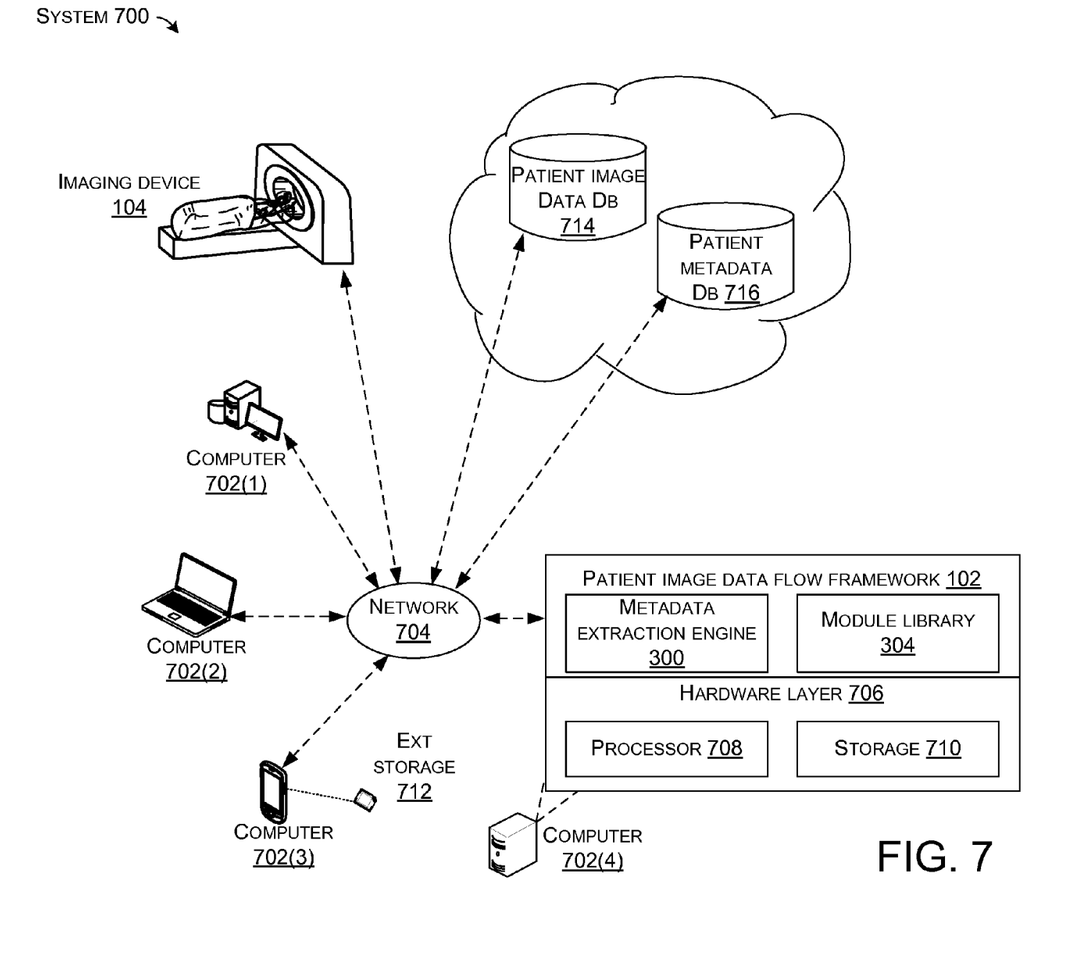
FIG. 7 shows a system upon which patient image data flow framework concepts can be employed in accordance with some implementations of the present concepts.

FIG. 7 shows an example of a system 700 that can provide the patient image dataflow framework and workflow methods discussed above. System 700 includes imaging device 104, patient image data flow framework 102, metadata extraction engine 300, and module library 304 which are introduced in the discussion above. System 700 also includes multiple computers 702(1)-702(4) that can communicate over a network 704. (The number of computers is selected for purposes of explanation and is not critical to the system or the inventive concepts). Imaging device 104 can also be considered a computer in some implementations. As illustrated relative to computer 702(4), patient image data flow framework 102 can include the metadata extraction engine 300 and the module library 304. The computers can also include or interact with a hardware layer 706 that can include a processor 708 and storage 710 (illustrated relative to computer 702(4)) and/or external storage 712 (illustrated relative to computer 702(3)). System 700 can also include a patient image data database 714 and a patient metadata database 716. These databases 714 and 716 can be freestanding, can be cloud-based, and/or can be associated with one or more of computers 702(1)-702(4).

The patient image data flow framework 102 can be configured to provide a data workflow pipeline to accomplish a task related to patient image data. The patient image data flow framework can implement an instance of the data workflow pipeline responsive to an event trigger and eliminate that instance of the workflow pipeline upon receipt of an event completion trigger.

The metadata extraction engine 300 can be configured to determine a set of modules to cooperatively accomplish the task. The metadata extraction engine can be configured to determine an order in which to arrange individual members of the set of modules along the data workflow pipeline. Viewed from one perspective, the metadata extraction engine can be configured to identify a module that has an output that can satisfy the task. The metadata extraction engine can examine the input requirements of this module and work backwards to select modules for the set that can satisfy the input requirements. In this implementation, the module library can contain a listing of the available modules, their functionality, and their input and output. These aspects are described above relative to FIG. 3.

The metadata extraction engine 300 can be configured to assign priorities to tasks. For example, multiple tasks may be incomplete at any given time and/or task completion may compete for other computing resources, such as processing cycles and cache storage. The metadata extraction engine can manage multiple data workflow pipeline instances in parallel to accomplish tasks consistent with their task priority. In some implementations, this task management aspect is dynamic so that data workflow pipelines can be reprioritized while processing is ongoing. In some cases, the task management aspect can be applied to processing resources and to memory allocation upon completion of the processing. For example, the metadata extraction engine may locally save (cache) the image and metadata produced by an individual data workflow pipeline instance so that subsequent queries for that data will not require recompilation.

The patient image data flow framework 102 can facilitate functioning of the data workflow pipeline by communicatively coupling the set of modules in the determined order to allow the task to be accomplished. Viewed from one perspective, the patient image data flow framework can supply the proper input of patient image data and associated metadata to the first module and then supply output metadata from that module to the next module along with any other information, such as the patient image data to the next module, and so forth for the set of modules.

System 700 can represent a web-based implementation where the functionality offered by the patient image data flow framework is provided on computer 702(4) that is remote from the user's computers 702(1)-702(3). The results of the patient image data flow framework can then be presented to the users on computers 702(1)-702(3). Alternatively, system 700 can be a distributed system where some of the patient image data flow framework functionality is provided locally and some of the functionality is provided remotely. For instance, the metadata extraction engine 300 could run on computer 702(1) while the other components run on computer 702(4). In still another configuration, a fully functioning patient image data flow framework could operate on each computer. These components could then access and update the patient image data database 714 and the patient metadata database 716. Alternatively or additionally, the patient image data flow framework could be a pluggable mechanism whereby services can be packaged and installed on servers by different parties. Further still, the metadata extraction engine can manage individual modules of the data workflow pipeline operating at different locations. For example, a single metadata extraction engine could control and communicatively couple a first module operating on computer 702(1) and a second module operating on computer 702(2). Further, while distinct computing devices are illustrated, some implementations can be performed at least in part utilizing cloud-based resources, the location of which may not be readily apparent.

The metadata extraction engine 300 can also be data and/or resource aware relative to reducing data movement. For instance, assume that imaging device 104 has 100 gigabytes of patient image data and underutilized computing resources. Assume further that a first module of a data workflow pipeline constructed by the metadata extraction engine is 10 megabytes. Rather than sending the patient image data from the imaging device to a computer, such as computer 702(4) upon which a first module is operating, the metadata extraction engine can send an instance of the first module to the imaging device 104 to process the patient image data and produce associated metadata. This associated metadata can then be sent to patient metadata database 716 and another computer, such as computer 702(4) upon which a second module is operating that utilizes the metadata as input. This data awareness may decrease the total amount of data that is communicated over the network 704 and/or take advantage of under-utilized computing resources within the system 700.

The term "computer" or "computing device" as used herein can mean any type of device that has some amount of processing capability and/or storage capability. Processing capability can be provided by one or more processors (such as processor 708) that can execute data in the form of computer-readable instructions to provide a functionality. Data, such as computer-readable instructions, can be stored on storage 710 or 712. The storage can include any one or more of volatile or non-volatile memory, hard drives, flash storage devices, and/or optical storage devices (e.g., CDs, DVDs etc.), among others. As used herein, the term "computer-readable media" can include transitory and non-transitory computer-readable instructions. In contrast, the term "computer-readable storage media" excludes transitory instances. Computer-readable storage media includes "computer-readable storage devices". Examples of computer-readable storage devices include volatile storage media, such as RAM, and non-volatile storage media, such as hard drives, optical discs, and flash memory, among others.

Examples of computing devices can include traditional computing devices, such as personal computers, cell phones, smart phones, personal digital assistants, or any of a myriad of ever-evolving or yet to be developed types of computing devices. Further, aspects of system 700 can be manifest on a single computing device or distributed over multiple computing devices.

Conclusion

Although techniques, methods, devices, systems, etc., pertaining to patient image data workflow are described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

The invention claimed is:

1. A method performed by at least one computer, the method comprising:
   determining a set of modules for collectively producing specific information related to image data based on comparing known inputs and outputs of the modules of the set;
   retrieving the set of modules from a library;
   arranging the set of modules in an image data workflow pipeline responsive to receiving an event trigger; and
   obtaining the specific information by directing the image data to the image data workflow pipeline to be processed by the set of modules, directing the image data to the patient image data workflow comprising:
   determining whether to send the image data to a first device having a module of the set of modules or send an instance of the module to a second device having the image data to process the image data based at least in part on a data size of the image data and a data size of the module, the determining reducing an amount of data to be communicated; and
   causing the first device having the module to send the instance of the module to the second device having the image data to process the image data to produce associated metadata in response to determining that the instance of the module is to be sent to the second device having the image data to process the image data, wherein the second device having the image data sends the associated metadata to a third device having another module that uses the associated metadata as an input.

2. The method of claim 1, wherein the set of modules are arranged temporarily and serially, and the arranging comprises:
   supplying the image data to a first module of the set of modules to obtain region labels; and
   communicatively coupling the region labels that are output by the first module as input to a second module.

3. The method of claim 1, further comprising removing the set of modules from the image data workflow pipeline responsive to receiving an event completion trigger.

4. A system comprising:
   one or more hardware processors;
   memory;
   a metadata extraction engine stored in the memory and executable by the one or more hardware processors to:
   select a set of modules from a module library to cooperatively accomplish a task related to image data based on comparing known input and output information of modules in the module library in response to receiving an event trigger,
   determine whether to send the image data to a first device having a module of the set of modules or send an instance of the module to a second device having the image data to process the image data based at least in part on a data size of the image data and a data size of the module, the determining reducing an amount of data to be communicated,
   cause the first device having the module to send the instance of the module to the second device having the image data to process the image data to produce associated metadata in response to determining that the instance of the module is to be sent to the second device having the image data to process the image data, wherein the second device having the image data sends the associated metadata to a third device having another module that uses the associated metadata as an input; and
   an image dataflow framework stored in the memory and executable by the one or more hardware processors to provide a data workflow to perform the task on the image data by causing an execution of the set of modules in a specific sequence.

5. The system of claim 4, wherein the metadata extraction engine is further configured to:
   obtain region labels from a first module of the set of modules; and
   provide the region labels to a second module of the set of modules.

6. The system of claim 4, wherein the metadata extraction engine is configured to:
   evaluate the module library to determine metadata output information by individual modules of the module library; and
   determine an order in which to arrange the set of modules based upon the metadata output information by the individual modules.

7. The system of claim 4, wherein the metadata extraction engine is further configured to communicatively couple individual modules of the set of modules in series to accomplish the task, disconnect the individual modules upon completion of the task, and then select a new set of modules to accomplish another task.

8. The system of claim 4, wherein the metadata extraction engine is further configured to select multiple sets of modules to accomplish multiple tasks and prioritize execution of the multiple tasks.

9. The system of claim 8, wherein the metadata extraction engine is further configured to reprioritize the multiple tasks during the execution.

10. The system of claim 4, wherein the system is embodied on a single computing device.

11. The system of claim 4, wherein the system is embodied on cloud-based computing resources and wherein the system is further configured to generate a web-based interface which allows one or more users to specify the task.

12. The system of claim 4, wherein the image dataflow framework and the metadata extraction engine are manifest on a first computing device and wherein the metadata extraction engine is further configured to send results of the task to another computing device upon which a user requests the results.

13. A system comprising:
one or more hardware processors; and
computer-readable storage media storing computer-readable instructions which, when executed by the one or more hardware processors, cause the one or more hardware processors to perform acts comprising:
receiving a trigger to perform a task on input data to produce a specified task output type;
accessing a module library that identifies respective input and output information of a plurality of modules;
analyzing the module library to select a specific sequence of modules from the module library to arrange in a workflow for performing the task;
determining whether to send the input data to a module of the specific sequence of modules or send an instance of the module to a device having the input data to process the input data based at least in part on a data size of the input data and a data size of the module, the determining reducing an amount of data to be communicated;
sending the instance of the module to the device having the input data to process the input data to produce associated metadata, wherein the device having the input data sends the associated metadata to another device having another module that uses the associated metadata as an input; and
causing the workflow to perform the task on the input data by executing the modules of the workflow in the specific sequence.

14. The system of claim 13, wherein the acts further comprise:
tagging regions of the input data with region tags using one of the modules of the workflow; and
tagging structures within an individual region of the input data with structure tags using another one of the modules of the workflow.

15. The system of claim 14, wherein the specified task output type comprises the structure tags.

16. The system of claim 15, wherein the input data comprises an image.

17. The system of claim 16, wherein the image comprises an image of a patient, the region tags identify anatomical regions in the image, and the structure tags identify anatomical structures in a particular anatomical region.

18. The system of claim 17, wherein the particular anatomical region is a thorax of the patient, and an individual structure tag identifies a lung of the patient in the image.

* * * * *